United States Patent
Hashmi et al.

(10) Patent No.: US 9,707,021 B2
(45) Date of Patent: Jul. 18, 2017

(54) VARIABLE ANGLE LOCKING ROTATION CORRECTION PLATE

(71) Applicant: DePuy Synthes Products, Inc., Raynham, MA (US)

(72) Inventors: Adam Hashmi, West Chester, PA (US); Lynn Kelly, West Chester, PA (US); Daneen Touhalisky, West Chester, PA (US); Thomas J. Fischer, Indianapolis, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 446 days.

(21) Appl. No.: 14/320,525

(22) Filed: Jun. 30, 2014

(65) Prior Publication Data

US 2015/0374423 A1 Dec. 31, 2015

(51) Int. Cl.
*A61B 17/88* (2006.01)
*A61B 17/80* (2006.01)

(52) U.S. Cl.
CPC .................. *A61B 17/8061* (2013.01)

(58) Field of Classification Search
None
See application file for complete search history.

(56) References Cited

U.S. PATENT DOCUMENTS

| 2,800,818 | A | * | 7/1957 | Larson | .................. B21D 11/10 |
| | | | | | 206/223 |
| 102,775 | A1 | | 5/2004 | Huebner | |
| 217,327 | A1 | | 8/2010 | Vancelette et al. | |
| 165,979 | A1 | | 6/2013 | Greenberg et al. | |
| 2012/0109216 | A1 | | 5/2012 | Austin et al. | |

FOREIGN PATENT DOCUMENTS

| DE | 202005019277 | 2/2006 |
| EP | 2476388 | 7/2012 |
| EP | 2623059 | 8/2013 |
| WO | 2005/046494 | 5/2005 |

* cited by examiner

*Primary Examiner* — Sameh Boles
(74) *Attorney, Agent, or Firm* — Fay Kaplun & Marcin, LLP

(57) ABSTRACT

A bone plate sized and shaped for fixation to one of a phalangeal and metacarpal bone includes a head extending from a first end to a second end and having an elongated curved plate hole extending therethrough along a curved path from a first end to a second end, a plate hole axis of the elongated curved plate hole extending orthogonally from a top surface to a bone contacting surface of the bone plate and a shaft extending from the head, the shaft including an elongated shaft plate hole extending therethrough and elongated in a direction extending orthogonal to a central longitudinal axis of the bone plate, a plate hole axis of the elongated shaft plate hole extending orthogonally from the top surface to the bone contacting surface.

17 Claims, 2 Drawing Sheets

VARIABLE ANGLE LOCKING ROTATION CORRECTION PLATE

FIELD OF THE INVENTION

The present invention generally relates to bone plates for the fixation of fractures of the hand and methods of coupling these plates to bone.

BACKGROUND

Many current systems and methods for the fixation of fractures, especially fractures in the hand, are limited in the placement and orientation of plates over the bone. For example, a surgeon or other user may be required to select a final placement position of the bone plate prior to beginning a bone reduction procedure. Such plates may prevent the surgeon from selecting the most optimal implantation location for the bone plate. Furthermore, such plates may prevent the fixation of a fractured or otherwise damaged bone in a manner to fully correct the alignment of one or more bone fragments. Rather, such fragments must be brought as close to a final configuration as possible prior to the placement of the bone plate thereover, which may result in subsequent misalignment as the bone plate is being secured to the bone. Rotational misalignments are especially problematic due to crossing and scissoring of the digits when a full flexion of the fingers (e.g., making a fist) is attempted. Even minor rotational errors in the fingers may have to be surgically corrected after a fracture has healed. Furthermore, this method of insertion may also compromise adjacent soft tissue.

SUMMARY OF THE INVENTION

The present invention is directed to A bone plate sized and shaped for fixation to one of a phalangeal and metacarpal bone, comprising a head extending from a first end to a second end and having an elongated curved plate hole extending therethrough along a curved path from a first end to a second end, a plate hole axis of the elongated curved plate hole extending orthogonally from a top surface to a bone contacting surface of the bone plate and a shaft extending from the head, the shaft including an elongated shaft plate hole extending therethrough and elongated in a direction extending orthogonal to a central longitudinal axis of the bone plate, a plate hole axis of the elongated shaft plate hole extending orthogonally from the top surface to the bone contacting surface.

BRIEF DESCRIPTION OF THE DRAWINGS

Several embodiments of the invention will be described in the following by way of example and with reference to the accompanying drawings in which.

DETAILED DESCRIPTION

Figure 1:
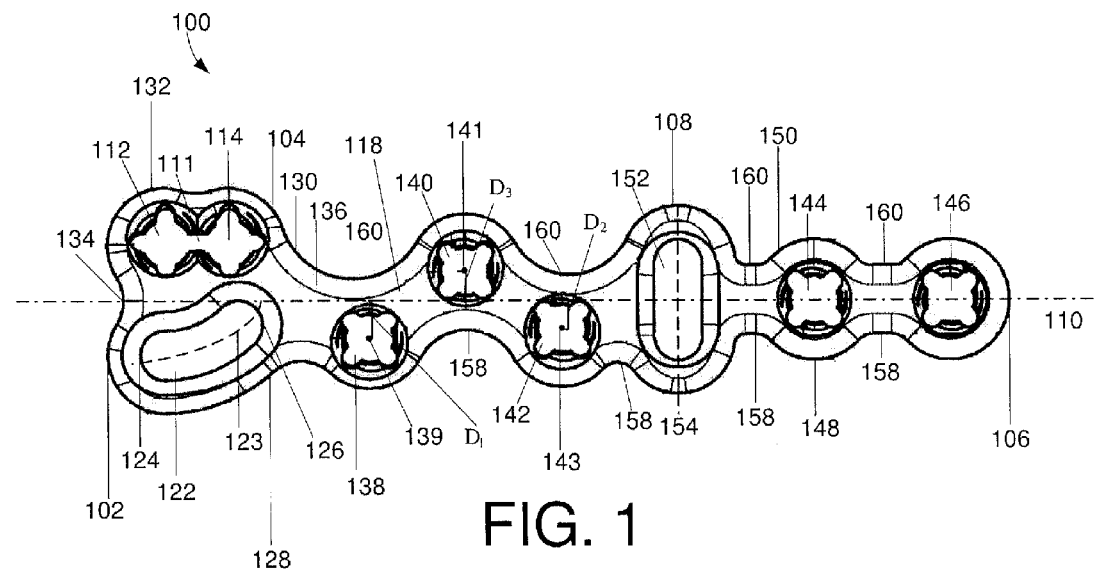
FIG. 1 shows a top view of a bone fixation plate according to a first exemplary embodiment of the invention.
Figure 2:
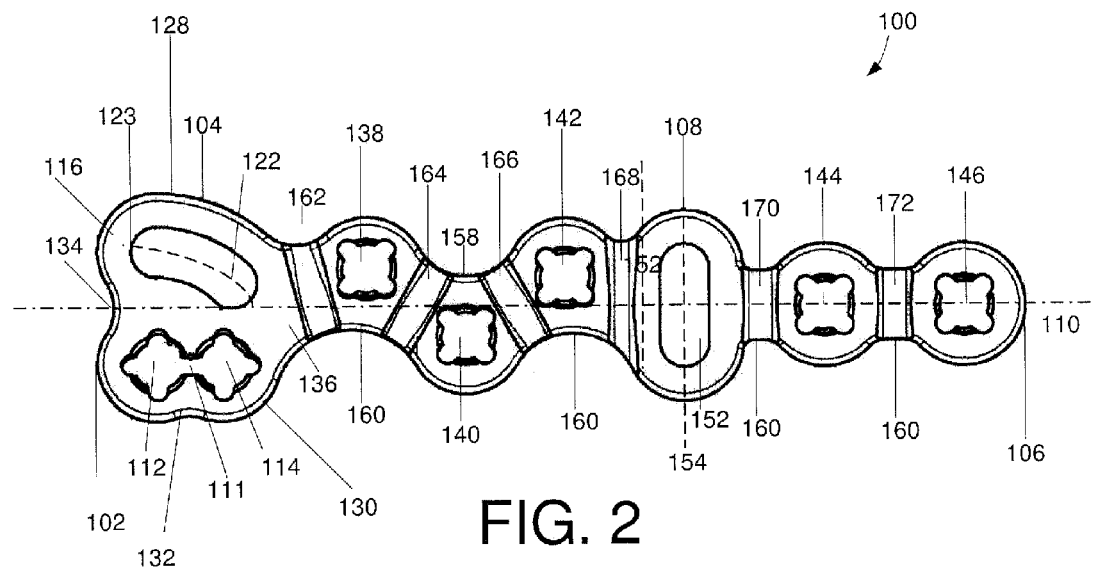
FIG. 2 shows a bottom view of the bone fixation plate of FIG. 1.
Figure 3:
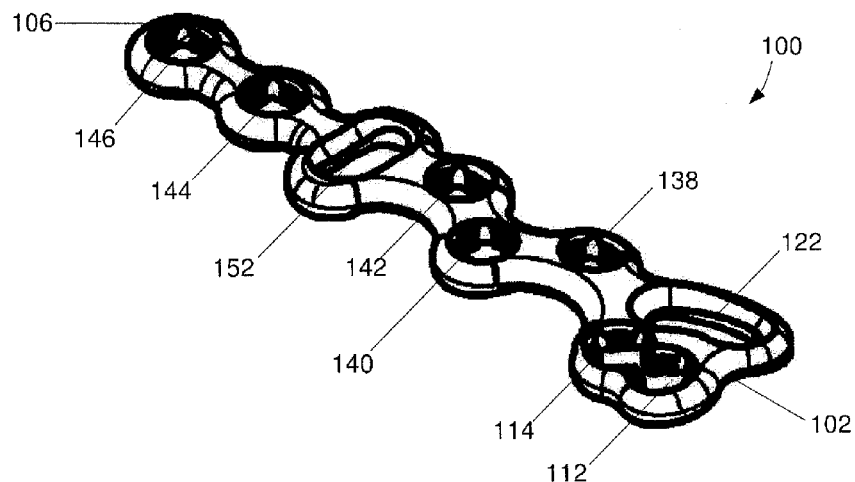
FIG. 3 shows a perspective view of the bone fixation plate of FIG. 1.

The exemplary embodiments may be further understood with reference to the following description and the appended drawings, wherein like elements are referred to with the same reference numerals. The exemplary embodiments relate to apparatus and methods for the treatment of fractures and, in particular, to devices for fixing fractures of the metacarpals and phalanges. Exemplary embodiments describe a bone fixation plate having a head at a first end with an elongated shaft extending therefrom to a second end. The head of the exemplary bone plate includes first and second variable angle fixation holes along a first side thereof. The head also includes an elongated curved hole extending along a second side thereof. The elongated curved hole permits rotation and angulation of the bone plate about a cortex screw inserted therethrough as will be described in more detail below. The shaft includes third, fourth and fifth plate holes staggered about a central longitudinal axis of the bone plate and an elongated plate hole extending along an axis orthogonal to the central longitudinal axis. As will be described in greater detail later on, the elongated hole further aids in optimally positioning the plate over a target portion of the bone. The shaft further may comprise sixth and seventh variable angle locking holes at a second end thereof. The sixth and seventh holes are aligned with the central longitudinal axis. A bone contacting surface of the head has a curvature selected to conform to a curvature of a dorsal surface of a bone to ensure flush seating of the plate thereover. As will be described in greater detail later on, the exemplary curved and elongated plate holes permit the adjustment of rotation and angulation of the bone plate prior to a final fixation of the bone plate to the bone.

Figure 4:
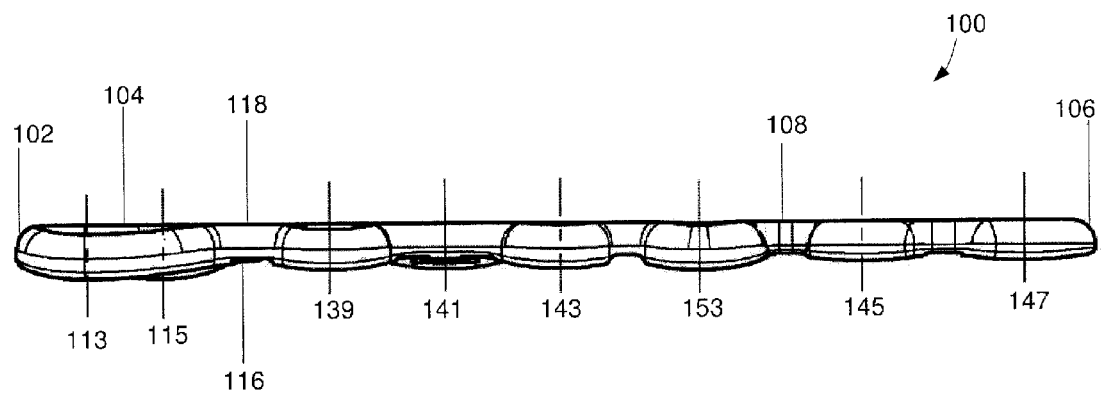
FIG. 4 shows a side view of the bone fixation plate of FIG. 1.

As shown in FIGS. 1-4, an exemplary bone plate 100 has a head 104 at a first end 102 thereof and a shaft 108 extending therefrom generally along a central longitudinal axis 110 to a second end 106. The head 104 includes first and second variable angle plate holes 112, 114 extending therethrough from a bone contacting surface 116 to an upper surface 118, the first and second plate holes 112, 114 being open to one another at an opening 111. Trajectories for plate hole axes 113, 115 of the first and second plate holes 112, 114 are selected to capture common fracture patterns while avoiding the articular surface of the bone and minimizing interference with adjacent collateral ligaments. As shown in FIG. 4, the plate hole axes 113, 115 may be generally orthogonal to the top surface 118 while the variable angle feature of the plate holes 112, 114 permits a surgeon to vary an angle at which screws are inserted through these holes (relative to the hole axes) to optimize these trajectories to suit the anatomy of a particular patient.

The head 104 further comprises an elongated curved plate hole 122 extending from a first end 124 to a second end 126 along a curved arc-shaped axis 123. A length of the plate hole 122 between the first and second ends 124, 126 is greater than a diameter of the first and second plate holes 112, 114. A width of the plate hole 122 is equivalent to a diameter of the first and second plate holes 112, 114. A length of the plate hole 122 may be equivalent to or slightly longer than a length of a combination of the first and second plate holes 112, 114. The first and second plate holes 112, 114 and the curved plate hole 122 may be sized, shaped and positioned along the head 104 to maximize the amount of area for screw placement while minimizing the foot print of the head 104 and maintaining strength of the plate 100.

A radius of curvature of the plate hole 122 may be, for example, 3.75 mm or 5.0 mm, although other values are depicted within the scope of the invention. A center from which the radius of curvature of the plate hole 122 may be measured may be located through, for example, the first plate hole 112. The curved plate hole 122 follows a bananalike curvature, curving toward the central longitudinal axis 110 so that the first end 124 is further from the axis 110 than is the second end 126. The exemplary curvature of the elongated curved plate hole 122 permits the bone plate to slide along the curve about a bone screw inserted therethrough. Specifically, the bone screw (not shown) may be inserted into the elongated curved plate hole 122 at a position selected to capture one or more bone fragments. The bone screw (not shown) may be inserted through the bone plate 100 and bone (not shown) to a first depth permitting the bone plate 100 to be movable about the bone screw. Subsequent sliding of the bone plate 100 along the axis 123 moves the bone plate 100 along a curved path corresponding to the path 123 as the bone plate 100 is moved in first and second directions along the central longitudinal axis 110. Furthermore, a surgeon or other user may rotate the bone plate 100 about the bone screw (not shown) received in the elongated plate hole 122 to achieve a desired orientation over the bone, as will be described in greater detail with respect to the exemplary method below. As phalange and metacarpal fractures typically result in a breakage of the "head" or "condyle" to a smaller fragment, the curved plate hole 122 located in the head 104 permits the surgeon or other user to affix the head 104 of the plate 100 to that smaller fragment first, and then would have the ability to rotate the plate to fit the shaft.

An outer surface of the head 104 substantially follows a position of the first, second and elongated plate holes 112, 114, 122. Specifically, a first side wall 128 of the head 104 follows a curved path corresponding to a curvature of the elongated plate hole 122. A second side wall 130 of the head 104 is also curved to conform to the shape of the first and second plate holes 112, 114, the size and curvature of the second wall 130 being formed so that a minimum clearance is formed about the first and second plate hole 112, 114. A first notch 132 is formed on the second side wall 130 of the head 104 and has a substantially rounded shape. The first notch 132 is formed as a cutout extending into the second side wall 130 and has a shape corresponding to an arc of a circle. In another embodiment, the first notch 132 may have a non-circular shape (e.g., oblong, etc.) without deviating from the scope of the invention. The first end 102 of the bone plate 100 also comprises a second notch 134 positioned between the first and elongated plate holes 112, 122, the second notch 134 also having a substantially rounded shape. In one embodiment, the second notch 134 has a radius of curvature of 1.5 mm or 2.0 mm. However, this radius of curvature is exemplary only and other values may be used without deviating from the scope of the invention. The second notch 134 is centered with respect to the central longitudinal axis 110 of the bone plate. In another embodiment, the second notch 134 may have a non-circular shape (e.g., oblong, etc.) without deviating from the scope of the invention. The first and second notches 132, 134 also effectively reduce an outer profile of the bone plate 100 without compromising the structural integrity thereof.

The bone-contacting surface 116 of the bone plate 100 is curved to conform to the curvature of a target dorsal surface of a metacarpal or phalangeal bone. In one embodiment, the bone-contacting surface 116 of the head 104 includes curvatures of varying radii. A predetermined length of the head 104 at the first corner 122 may be curved downward toward the bone in a direction toward a palmar surface of the bone in an implanted configuration. This downward curvature aids in reduction of the fracture.

A reduced diameter neck 136 separates the head 104 from the shaft 108. The shaft 108 extends distally from the neck 136 to the distal end 106 and includes third, fourth, fifth, sixth and seventh variable angle plate holes 138, 140, 142, 144, 146. In one embodiment, trajectories 139, 141, 143, 145, 147 of the third, fourth, fifth, sixth and seventh place holes 138, 140, 142, 144, 146 are orthogonal to a plane housing the bone plate 100 while the variable angle features thereof permit a surgeon to vary the angles at which screws are inserted therethrough to optimize these trajectories to suit the anatomy of a particular patient. Thus, the trajectories 139, 141, 143, 145, 147 may assume any path selected to lockingly engage the bone without extending through an opposing cortical surface thereof. The third, fourth and fifth plate holes 138, 140, 142 are staggered about the central longitudinal axis 110 so that central axes 139, 141, 143 thereof are offset relative to the axis 110. The staggered shaft portion of the plate 100 increases plate strength and allows for distribution of bone screws over a larger surface area of the bone to capture fracture fragments in a comminuted shaft, as those skilled in the art will understand. Specifically, the third and fifth plate holes 138, 142 are offset in a first direction toward a first side wall 148 of the shaft 108. Specifically, the third and fifth plate holes 138, 142 extend away from the axis 110 in the first direction by a distance greater than any other portion of the shaft 108. In a preferred embodiment, the central axis 139 of the third plate hole 138 is separated from the axis 110 by a distance $D_1$ and the central axis 143 of the fifth plate hole 142 is separated from the axis 110 by a distance $D_7$, wherein $D_1$ is greater than $D_2$. The fourth plate hole 140 is offset in a second direction toward a second side wall 150 of the shaft 108 so that a distance $D_3$ is formed between a central axis 141 of the fourth plate hole 140 and the axis 110. The distances $D_2$ and $D_3$ may be substantially equivalent to one another. The central axes 141, 143 of the fourth and fifth plates holes 140, 142, respectively, may be closer to the axis 110 than the central axis 139 of the third plate hole 138 since the phalanges and metacarpals become thinner towards a central portion thereof. It will be understood by those of skill in the art, however, that $D_1$ is not required to be greater than $D_2$ and $D_3$, so long as the third, fourth and fifth holes 138, 140, 142 are positioned through the plate 100 so that, when the plate 100 is positioned along a bone, the third, fourth and fifth holes 138, 140, 142 extend along a portion of the bone. It will also be understood by those of skill in the art that although the exemplary embodiment shows the third and fifth holes 138, 142 as offset from the axis 110 in the first direction towards the first side wall 148 and the fourth plate hole 140 is offset from the axis 110 in the second direction toward the second side wall 150, a direction in which the third, fourth and fifth holes 138, 140, 142 are offset may also be reversed. In particular, the third and fifth holes 138, 142 may be offset in the second direction while the fourth hole 140 may be offset in the first direction.

The shaft 108 also includes an elongated hole 152 elongated in a direction orthogonal to the longitudinal axis 110. The elongated hole 152 is centered about the central longitudinal axis 110, a trajectory 153 thereof extending orthogonally from the bone contacting surface 116 to the top surface 118. An axial length of the elongated hole 130 is at least larger than a diameter of the first through seventh plate holes 112, 114, 138, 140, 142, 144, 146 while a width of the elongated hole 152 may be equivalent to the diameter of first through seventh plate holes 112, 114, 138, 140, 142, 144, 146. In a preferred embodiment, the first through seventh plate holes 112, 114, 138, 140, 142, 144, 146 are 1.5 mm variable angle holes. However, in another embodiment, one or more of the first through seventh plate holes 112, 114, 138, 140, 142, 144, 146 may be formed as standard locking holes having a diameter of 2.0 mm. Still further, it is noted that any other diameter of the holes may be used without deviating from the scope of the invention to conform to the requirements of a particular procedure. As will be described in greater detail below with respect to the exemplary method, the elongated hole 130 permits a surgeon or other user to slide the bone plate 100 over the bone within a predetermined range (i.e., corresponding to a length of the elongated hole 152) prior to locking the bone plate 100 in place. In one embodiment, the elongated hole 130 may allow for a movement of the bone plate along an axis 154 while also permitting rotation of the bone plate 100 therearound. Specifically, a surgeon or other user may insert a first bone screw into one of the elongated holes 122, 152 to affect a position of the bone plate 100 over the bone, as will also be described in greater detail later. The exemplary elongated plate hole 152 extends orthogonally through the bone plate from the upper surface 118 to the bone contacting surface 116. The elongated holes 122, 152 bypass the need for a guidewire to position the bone plate 100 over the bone. Rather, since the bone plate 100 is adjustable relative to a bone screw inserted through the elongated hole 122, 152, a surgeon or other user may use the elongated holes 122, 152 as a guide when positioning the bone plate 100 over the bone.

The sixth and seventh holes 144, 146 are axially aligned and symmetrically positioned relative to the central longitudinal axis 110.

The bone-contacting surface 116 of the shaft 108 is curved along the longitudinal axis 110 to conform to the substantially cylindrical shape of the target portion of the bone over which the shaft 108 will be seated. In one embodiment, the length of the shaft 108 may include a single uniform curvature. In another embodiment, the bone contacting surface 116 of the shaft 108 may include a plurality of curves selected to ensure that the shaft 108 is seated flush over the bone.

The shaft 108 also includes a plurality of first webbed portions 158 extending along the first side wall 148 between each of the holes 138, 142, 144, 146 and a plurality of second webbed portions 160 extending along the second side wall 150 between each of the holes 114, 140, 152, 144, 146. The first and second webbed portions 158, 160 are formed as notches extending into the width of the bone plate 100 reducing a profile thereof while maintaining the structural integrity of the bone plate 100. The first and second webbed portions 158, 160 as well as the first and second notches 132, 134 are sized to maintain a minimum desired clearance remains around the boundary of each of the plate holes of the bone plate 100. An outer periphery of the bone plate 100 may include a rounded taper to further reduce the profile as would be understood by those skilled in the art.

The bone-contacting surface 116 of the bone plate further comprises a plurality of undercuts 162, 164, 166, 168, 170, 172 positioned between plate holes to permit bone ingrowth while also imparting additional flexibility to the bone plate 100 to permit a surgeon to further bend the bone plate 100 to a desired curvature to more closely match the anatomy of a patient's bone and promote healthier bone ingrowth. The undercuts 162, 164, 166, 168, 170, 172 are formed as cutouts extending into the bone plate 100 from the bone-contacting surface 116 by a depth smaller than a thickness of the bone plate 100. In a preferred embodiment, a shape of the cutouts is a half-cylindrical segment, although other shapes (e.g., rectangular, etc.) may be used without deviating from the scope of the invention. First, second and third undercuts 162, 164, 166 are angled with respect to the axis 110 in accordance with a position of the third, fourth and fifth plate holes 138, 140, 142. Specifically, the first undercut 162 encloses an angle of 105° relative to the axis 110. The second undercut 164 encloses an angle of 60° relative to the axis 110. The third undercut 166 encloses an angle of 120° relative to the axis 110. Fourth, fifth and sixth undercuts 168, 170, 172 extend orthogonally to the axis 110.

The exemplary bone plate 100 is configured for use in indirect reduction techniques for crushes, multi-fragmented and/or periarticular fractures of the metacarpals and phalanges. In accordance with an exemplary method according to the invention, the bone plate 100 is positioned over a target dorsal surface of a bone in a target orientation so that the elongated curved plate hole 122 is positioned adjacent a far side of a fracture near a section of intact bone. The surgeon or other user approximates the desired position of the bone plate 100 over the bone. A first cortex screw (not shown) is then inserted through the elongated curved hole 122 and into the bone to a first depth sufficient to hold the bone plate 100 over the bone while still permitting movement of the bone plate 100 relative to the bone. The bone plate 100 is then slid along the axis 123 about the first cortex screw (not shown) received in the hole 122 until a desired position has been reached. The first cortex screw (not shown) may be tightened and loosened a plurality of times during this repositioning. A second cortex screw (not shown) is then inserted into the elongated hole 152 to the first depth sufficient to hold the bone plate 100 over the bone while still permitting movement of the bone plate 100 relative to the bone. The bone plate 100 is then repositioned along the axis 154 to a desired final configuration. The first and second cortex screw (not shown) may be tightened and loosened a plurality of times during the above repositioning. The exemplary bone plate 100 according to the invention allows for an adjustment of rotation and angulation of the bone plate 100 prior to a permanent fixation thereof over the bone. Once the target position has been reached, additional screws (not shown) may be inserted into any of the remaining plate holes 112, 114, 138, 140, 142, 144, 146. The exemplary system and method according to the invention bypasses the need for pre-drilling holes in the bone. Rather, once the target position has been achieved, bore holes are drilled through any of the plate holes 112, 114, 138, 140, 142, 144, 146 and into the bone at a desired angle selected to conform to the requirements of the particular bone. In contrast, present bone fixation systems require the insertion of a guidewire into the bone prior to the placement of the bone plate over the bone, thus requiring that a final position of the bone plate 100 be selected prior to the placement of the bone plate over the bone. This method may lead to reduced accuracy in placement, especially in the fixation of phalangeal bones where even the smallest deviation, (e.g., in millimeters) from a correct position may lead to less than optimum fixation. The exemplary bone plate 100, on the other hand, permits adjustment of the position of the bone plate 100 even after the bone plate 100 has been initially secured to the bone, thereby ensuring that the final position of the bone plate 100 captures all fragments of the bone while avoiding interference with ligaments, tendons or other tissue.

It will be appreciated by those skilled in the art that various modifications and alterations of the disclosed embodiments may be made without departing from the broad scope of the invention. Some of these have been discussed above and others will be apparent to those skilled in the art.

What is claimed is:

1. A bone plate sized and shaped for fixation to one of a phalangeal and metacarpal bone, comprising:
   a head extending from a first end to a second end and having an elongated curved plate hole extending therethrough along a curved path from a first end to a second end, a plate hole axis of the elongated curved plate hole extending orthogonally from a top surface to a bone contacting surface of the bone plate; and
   a shaft extending from the head, the shaft including an elongated shaft plate hole extending therethrough and elongated in a direction extending orthogonal to a central longitudinal axis of the bone plate, a plate hole axis of the elongated shaft plate hole extending orthogonally from the top surface to the bone contacting surface.

2. The bone plate of claim 1, wherein the elongated curved plate hole is positioned on a first side of the central longitudinal axis.

3. The bone plate of claim 2, wherein the head includes first and second variable angle plate holes extending therethrough.

4. The bone plate of claim 3, wherein the first and second variable angle plate holes are open to one another.

5. The bone plate of claim 4, wherein the first and second variable angle plate holes are positioned on a second side of the central longitudinal axis.

6. The bone plate of claim 3, wherein the head further comprises a first notch on the first end between the elongated curved plate hole and the first variable angle plate hole, the first notch formed as an indentation on an outer wall of the bone plate.

7. The bone plate of claim 6, wherein the head further comprises a second notch on a first side wall of the bone plate between the first and second variable angle plate holes.

8. The bone plate of claim 3, wherein the shaft further comprises third, fourth and fifth variable angle plate holes extending therethrough and positioned between the head and the elongated shaft plate hole.

9. The bone plate of claim 8, wherein the third, fourth and fifth plate holes are staggered about the central longitudinal axis so that third and fifth plate holes are located on a first side of the central longitudinal axis and the fourth plate hole is located on a second side of the central longitudinal axis.

10. The bone plate of claim 8, further comprising sixth and seventh variable angle plate holes extending therethrough and positioned between the elongated shaft plate hole and the second end of the bone plate.

11. The bone plate of claim 10, wherein the sixth and seventh plate holes are centered about the central longitudinal axis.

12. The bone plate of claim 2, wherein the elongated shaft plate hole is centered about the central longitudinal axis.

13. The bone plate of claim 1, further comprising a reduced diameter neck between the head and the shaft, a diameter of the neck being reduced relative to adjacent portions of the head and shaft.

14. The bone plate of claim 1, wherein the shaft includes a plurality of shaft notches formed in first and second side walls thereof, the shaft notches defining reduced width regions of the shaft.

15. The bone plate of claim 1, further comprising a plurality of undercuts extending into the bone contacting surface of the bone plate by a depth less than a thickness of the bone plate.

16. The bone plate of claim 1, further comprising a tapered region extending around a periphery of the bone plate to reduce a profile thereof.

17. The bone plate of claim 1, wherein a bone contacting surface of the head is contoured to conform to the anatomy of a dorsal surface of a head of the bone.

* * * * *